(12) United States Patent
Hewett

(10) Patent No.: US 6,660,692 B1
(45) Date of Patent: Dec. 9, 2003

(54) HERBICIDAL COMPOSITIONS COMPRISING PICOLINAFEN

(75) Inventor: Richard Henry Hewett, Ongar (GB)

(73) Assignee: Aventis CropScience S.A., Lyons (FR)

(*) Notice: Subject to any disclaimer, the term of this patent is extended or adjusted under 35 U.S.C. 154(b) by 0 days.

(21) Appl. No.: 10/018,395

(22) PCT Filed: Jun. 16, 2000

(86) PCT No.: PCT/EP00/06255

§ 371 (c)(1),
(2), (4) Date: Dec. 13, 2001

(87) PCT Pub. No.: WO00/78147

PCT Pub. Date: Dec. 28, 2000

(30) Foreign Application Priority Data

Jun. 17, 1999 (GB) .............................. 9914213

(51) Int. Cl.$^7$ ..................... A01N 35/06; A01N 37/34; A01N 41/10; A01N 43/40; A01N 47/30
(52) U.S. Cl. ................. 504/130; 504/138; 504/141; 504/256; 504/271; 504/310; 504/330
(58) Field of Search ................ 504/130, 138, 504/141, 256, 330, 310, 271

(56) References Cited

FOREIGN PATENT DOCUMENTS

| EP | 0 447 004 | * 9/1991 |
| EP | 0 878 128 | 11/1998 |
| WO | WO 94/07368 | 4/1994 |

* cited by examiner

*Primary Examiner*—S. Mark Clardy
(74) *Attorney, Agent, or Firm*—Frommer Lawrence & Haug LLP

(57) ABSTRACT

This invention provides a method for controlling the growth of weeds (i.e. undesired vegetation) at a locus which comprises applying to the locus a herbicidally effective amount of: (a) picolinfen, a phenoxypicolinamide derivative of formula (I); and (b) a partner herbicide, selected from isoxazole, dione, urea and hydroxybenzonitrile herbicide.

(I)

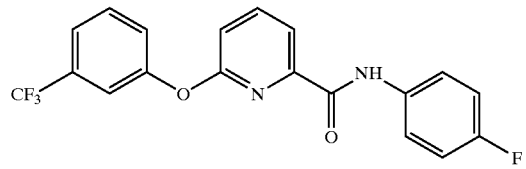

24 Claims, No Drawings

HERBICIDAL COMPOSITIONS COMPRISING PICOLINAFEN

The present invention relates to a method of controlling the growth of weeds by the application of a mixture of a phenoxypicolinamide compound and a partner herbicide; and to the compositions containing them.

Phenoxypicolinamide herbicides are disclosed in the literature, for example in European applications EP-A-878,128, EP-A-447,004 and WO 94/07368. Several classes of phenoxypicolinamide compounds are known, which include for example those substituted at the 2- and 3-positions of the phenoxy group. These two such classes are distinguished by the fact that previously only the 2-substituted compounds have been mixed with partner herbicides. Previously, in general it has not been suggested to prepare mixtures with the 3-substituted compounds.

However, it has now been discovered that there are specific herbicides which can be mixed with 3-substituted phenoxypicolinamide compounds.

However certain individual weed species constitute a serious problem and are insufficiently controlled by phenoxypicolinamide compounds. As a result of research and experimentation it has been found that the use of phenoxypicolinamide compounds in combination with one or more of these herbicides extends the spectrum of herbicidal activity. Therefore the said combination represents an important technological advance. The term "combination" as used in this specification refers to the "combination" of clomazone and diflufenican.

Surprisingly, it has been found that the combined herbicidal activity of phenoxypicolinamide compounds with one or more of these herbicides, for the control of certain weed species is greater than expected, without an unacceptable increase in crop phytotoxicity, when applied pre-emergence of the weed species, i.e. the herbicidal activity of phenoxypicolinamide compounds with one or more of these herbicides showed an unexpected degree of synergism, as defined by Limpel, L. E., P. H. Schuldt and D. Lamont, 1962, 1. Proc. NEWCC 16, 48–53, using the formula:

$$E = X + Y - \frac{X \cdot Y}{100}$$

where E=the expected percent inhibition of growth by a mixture of two herbicides A and B at defined doses.

X=the percent inhibition of growth by herbicide A at a defined dose.

Y=the percent inhibition of growth by herbicide B at a defined dose.

When the observed percentage of inhibition by the mixture is greater than the expected value E using the formula above the combination is synergistic. The unexpected synergistic effect gives improved reliability in controlling serious competitive weeds of many crop species, leading to a considerable reduction in the amount of active ingredient required for weed control.

Accordingly the present invention provides a method for controlling the growth of weeds (i.e. undesired vegetation) at a locus which comprises applying to the locus a herbicidally effective amount of:

(a) a phenoxypicolinamide derivative of formula I;

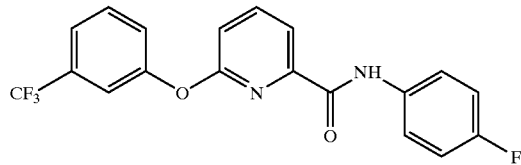

(I)

and (b) a partner herbicide selected from the group consisting of isoxazoles, diones, ureas and hydroxybenzonitrile (HBN) herbicides.

It will be understood that the herbicides used in the method of the invention may form agriculturally acceptable salts or metal complexes which may themselves be used in the method.

Advantageous possible partner herbicides for use in the present invention include;

isoxaflutole, which is 5-cyclopropyl-4-(2-methylsulphonyl-4-trifluoromethyl)-benzoylisoxazole, ketospirodox, which is 2-(2,3-dihydro-5,8-dimethyl-1,1-dioxospiro[4H-1-benzothiin-4,2'-[1,3]dioxolan]-6-ylcarbonyl)cyclohexane-1,3-dione and potassium salt, mesotrione, which is 2-(2'-nitro-4'-methylsulphonylbenzoyl)-1,3-cyclohexanedione, sulcotrione, which is 2-(2'-chloro-4'-methylsulphonylbenzoyl)-cyclohexane-1,3-dione, isoproturon, which is 3-(4-isopropylphenyl)-1,1-dimethylurea, bromoxynil, which is 3,5-dibromo-4-hydroxybenzonitrile and ioxynil, which is 4 hydroxy-3,5-di-iodobenzonitrile.

The preferred partner herbicides are chosen from isoxaflutole, isoproturon and bromoxynil.

The phenoxypicolinamide derivative of formula (I) and partner herbicides are normally used in the form of herbicidal compositions (i.e. in association with compatible diluents or carriers and/or surface-active agents suitable for use in herbicidal compositions), for example as hereinafter described.

The amounts of the phenoxypicolinamide derivative of formula (I) and partner herbicide applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates from 15 g to 1000 g/ha of the phenoxypicolinamide derivative of formula (I) and from 0.005 kg to 3 kg of partner herbicide per hectare give good results.

The phenoxypicolinamide derivative of formula (I) and a partner herbicide in combination may be used to control selectivity the growth of weeds, for example to control the growth of those species hereinafter mentioned, by pre- or post-emergence application in a directional or non-directional fashion, e.g. by directional or non-directional spraying, to a locus of weed infestation which is an area used, or to be used, for growing crops, for example cereals, e.g. barley, field and dwarf beans, carrots, cotton, flax, oats, lucerne, maize, oil seed rape, onions, peanuts, peas, rice, rye, soybeans, sunflower, wheat and permanent or sown grassland before or after sowing of the crop or before or after emergence of the crop. For the selective control of weeds at a locus of weed infestation which is an area used or to be used, for the growing of crops, e.g. the crops hereinbefore mentioned, application rates from 15 g to 500 g/ha of the phenoxypicolinamide derivative of formula (I) and from 250 g to 3000 g of urea herbicide; 5 g to 200 g isoxazole or dione herbicides; and from 50 g to 1000 g of HBN herbicide, per hectare are particularly suitable.

According to a feature of the present invention, there is provided a method for the control of the growth of weeds by pre- and/or post-emergence application which comprises the application of (a) a phenoxypicolinamide derivative of formula (I) and (b) a partner herbicide at application rates from 30 g to 200 g/ha of (a) and from 500 g to 2000 g/ha of urea herbicide, from 20 g to 100 g of isoxazole or dione herbicide; and from 20 0 g to 600 g (a.i.)/ha of the HBN herbicide, to control a very wide spectrum of annual broad-leafed weeds and grass weeds in cereal crops, e.g. barley, oats, rye and wheat without significant permanent damage to the crop. The combined use described above offers both foliar and residual activity and consequently can be employed over a long period of crop-development, i.e. from pre-weed pre-crop emergence to post-weed post-crop emergence. In the method according to this feature of the present invention, application of the herbicides to control weeds in autumn-sown cereals is preferred.

Weed species which are particularly well controlled include *Setaria viridis, Echinochloa crus-galli, Galium aparine, Abutilon theophrasti, Amaranthus retroflexus* and *Ipomoea purpurea*.

The phenoxypicolinamide derivative of formula (1) and a partner herbicide in combination may also be used to control the growth of weeds, especially those indicated below, by pre- or post-emergence application in established orchards and other tree-growing areas, for example forests, woods and parks, and plantations e.g. oil palm, rubber and sugar cane plantations. For this purpose they may be applied in a directional or non-directional fashion (e.g. by directional or non-directional spraying) to the weeds or to the soil in which they are expected to appear, before or after planting of the trees or plantations at application rates from 30 g to 1000 g, preferably from 100 g to 300 g of phenoxypicolinamide derivative of formula (I) and from 250 g to 3000 g of the urea herbicide, preferably from 500 to 2000 g; from 25 g to 500 g of an isoxazole or dione herbicide, preferably from 50 to 300 g; and from 100 g to 2000 g, preferably from 200 g to 1000 g of an HBN herbicide per hectare.

The phenoxypicolinamide derivative of formula (I) and a partner herbicide in combination may also be used to control the growth of weeds, especially those indicated below, at loci which are not crop-growing areas but in which the control of weeds is nevertheless desirable. Example of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described.

The precise dosage will depend upon the nature of the vegetation treated and the effect sought. Pre- or post-emergence application, preferably pre-emergence application, in a directional or non-directional fashion (e.g. by directional or non-directional spraying) at application rates from 15 g to 1000 g of the phenoxypicolinamide compound of formula (I) and from 0.005 kg to 3 kg of the partner herbicide per hectare are particularly suitable for this purpose.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. By the term "foliar activity" is meant herbicidal activity produced by application to the aerial or exposed portions of the weeds which have emerged above the surface of the soil. By the term "residual activity" is meant herbicidal activity produced by application to the soil in which weed seeds or seedling are present before emergence of the weeds above the surface of the soil, whereby seedling present at the time of application or which germinate subsequent to application from seeds present in the soil, are controlled.

Weeds that may be controlled by the method include:

*Alopecurus myosuroides, Anagallis arvensis, Anthemis arvensis, Anthemis cotula, Apera spica-venti, Aphanes arvensis, Arenaria serpyllifolia, Avena fatua, Bromus sterilis, Cerastium holosteoides, Chenopodium album, Chrysanthemum segetum, Descurainea sophia, Erysimum cheiranthoides, Galeopsis tetrahit, Galium aparine, Geranium dissectum, Geranium molle, Lamium amplexicaule, Lamium purpureum, Legousia hybrida, Lolium multiflorum, Lolium perenne, Matricaria inodora, Matricaria matricarioides, Montia Derfoliata, Myosotis arvensis, Papaver rhoeas, Phalaris minor, Phalaris paradoxa, Poa trivialis, Polygonum aviculare, Polygonum convolvulus, Silene vulgaris, Spergula arvensis, Stellaria media, Veronica hederifolia* and *Veronica Dersica*.

The pattern of persistence of the phenoxypicolinamide derivative of formula (I) and a partner herbicide allows the method of the present invention to be practised by the time-separated application of separate formulations.

The following non-limiting Examples illustrate the present invention:

EXAMPLE 1

Seeds of various broad-leaf and grass weed species may be sown and a mixture of the phenoxypicolinamide derivative of formula (I) and a partner herbicide, dissolved in water, applied to the soil surface. The said weeds comprise those listed above. Two weeks after treatment the percent reduction in plant growth, compared to an untreated control, may be assessed to reveal control in one or more weed species by compounds of formula (I) in combination with a partner herbicide.

EXAMPLE 2

Seeds of the various weed species, as listed above, may be sown and grown up to a 1–3 leaves stage, and a post-emergence application of a mixture of the phenoxypicolinamide derivative of formula (I) and a partner herbicide, dissolved in water, applied.

Two weeks after treatment the percent reduction in plant growth, compared to an untreated control, may be assessed to reveal control in one or more weed species by compounds of formula (I) in combination with a partner herbicide.

EXAMPLE 3

A glasshouse trial was carried out post-emergence in wheat using a tank mixture comprising a phenoxypicolinamide derivative of formula I (at 1, 4 and 16 g/ha) and isoproturon (at 125, 250 and 500 g/ha) which was sprayed on the following weed species:

Alopecurus myosuroides (ALOMY), Setaria viridis (SETVI), Avena fatua (AVEFA), Echinochloa crus-galli (ECHCG) and Galium aparine (GALAP).

Table 1 below shows the observed percentage control of the weed species by each compound and by the combination at 12 days after treatment, compared to the expected values calculated using the Colby formula shown in brackets.

TABLE 1

| Compound | Rate g ai/ha | Weed Species/% Weed Control | | | | |
|---|---|---|---|---|---|---|
| | | ALOMY | SETVI | AVEFA | ECHCG | GALAP |
| (I) | 1 | 10 | 10 | 10 | 10 | 10 |
| | 4 | 10 | 30 | 20 | 10 | 40 |
| | 16 | 30 | 70 | 40 | 40 | 90 |
| (II) | 125 | 0 | 50 | 0 | 10 | 0 |
| | 250 | 0 | 70 | 30 | 70 | 0 |
| | 500 | 20 | 100 | 30 | 70 | 0 |
| (I) + (II) | 1 + 125 | 10(10) | 70(55) | 50(10) | 50(19) | 20(10) |
| | 1 + 250 | 40(10) | 80(73) | 50(37) | 60(73) | 80(10) |
| | 1 + 500 | 40(28) | 100(100) | 70(37) | 100(73) | 80(10) |
| (I) + (II) | 4 + 125 | 10(10) | 80(65) | 70(20) | 60(19) | 100(40) |
| | 4 + 250 | 30(10) | 100(79) | 70(44) | 70(73) | 100(40) |
| | 4 + 500 | 70(28) | 100(100) | 70(44) | 95(73) | 100(40) |
| (I) + (II) | 16 + 125 | 70(30) | 100(85) | 70(40) | 95(46) | 80(90) |
| | 16 + 250 | 80(30) | 100(91) | 80(58) | 95(82) | 100(90) |
| | 16 + 500 | 80(44) | 100(100) | 90(58) | 100(82) | 100(90) |

Note: Compound (II) is isoproturon.

EXAMPLE 4

A glasshouse trial was carried out post-emergence in wheat using a tank mixture comprising a phenoxypicolinamide derivative of formula I (at 1, 4 and 16 g/ha) and bromoxynil (at 12.5, 50 and 200 g/ha) which was sprayed on the following weed species:

Setaria viridis (SETVI), Avena fatua (AVEFA), Echinochloa crus-galli (ECHCG) and Galium aparine (GALAP).

Table 2 below shows the observed percentage control of the weed species by each compound and by the combination at 12 days after treatment, compared to the expected values calculated using the Colby formula shown in brackets.

TABLE 2

| Compound | Rate (g ai/ha) | Weed Species/% Weed Control | | | |
|---|---|---|---|---|---|
| | | SETVI | AVEFA | ECHCG | GALAP |
| (I) | 1 | 10 | 10 | 10 | 10 |
| | 4 | 30 | 20 | 10 | 40 |
| | 16 | 70 | 40 | 40 | 90 |
| (III) | 12.5 | 0 | 0 | 0 | 0 |
| | 50 | 20 | 0 | 0 | 80 |
| | 200 | 20 | 10 | 20 | 100 |
| (I) + (III) | 1 + 12.5 | 50(10) | 50(10) | 40(10) | 40(10) |
| | 1 + 50 | 60(28) | 50(10) | 60(10) | 70(82) |
| | 1 + 200 | 60(28) | 60(19) | 60(28) | 100(100) |
| (I) + (III) | 4 + 12.5 | 40(30) | 50(20) | 50(10) | 100(40) |
| | 4 + 50 | 50(44) | 50(20) | 50(10) | 100(88) |
| | 4 + 200 | 60(44) | 60(28) | 70(28) | 100(100) |
| (I) + (III) | 16 + 12.5 | 70(70) | 70(40) | 60(40) | 100(90) |
| | 16 + 50 | 70(76) | 70(40) | 70(40) | 100(98) |
| | 16 + 200 | 80(76) | 70(46) | 80(52) | 100(100) |

Note: Compound (III) is bromoxynil.

EXAMPLE 5

A glasshouse trial was carried out post-emergence in wheat using a tank mixture comprising a phenoxypicolinamide derivative of formula I (at 1, 4 and 16 g/ha) and isoxaflutole (at 8, 16 and 32 g/ha) which was sprayed on the following weed species:

Alopecurus myosuroides (ALOMY) and Galium aparine (GALAP).

Table 3 below shows the observed percentage control of the weed species by each compound and by the combination at 12 days after treatment, compared to the expected values calculated using the Colby formula shown in brackets.

TABLE 3

| Compound | Rate g ai/ha | Weed Species/% Weed Control | |
|---|---|---|---|
| | | ALOMY | GALAP |
| (I) | 1 | 10 | 10 |
| | 4 | 10 | 40 |
| | 16 | 30 | 90 |
| (IV) | 8 | 10 | 60 |
| | 16 | 20 | 60 |
| | 32 | 40 | 80 |
| (I) + (IV) | 1 + 8 | 30(19) | 100(64) |
| | 1 + 16 | 30(28) | 100(64) |
| | 1 + 32 | 40(46) | 100(82) |
| (I) + (IV) | 4 + 8 | 10(19) | 100(76) |
| | 4 + 16 | 30(28) | 100(76) |
| | 4 + 32 | 60(46) | 100(88) |
| (I) + (IV) | 16 + 8 | 50(37) | 100(96) |
| | 16 + 16 | 50(44) | 100(96) |
| | 16 + 32 | 80(58) | 100(98) |

Note: Compound (IV) is isoxaflutole.

According to a further feature of the present invention, there are provided compositions suitable for herbicidal use comprising (a) a phenoxypicolinamide compound of formula (I) and (b) a partner herbicide selected from the group consisting of isoxazoles, diones, ureas and hydroxybenzonitriles (HBNs) in association with, and preferably homogeneously dispersed in, one or more compatible herbicidally-acceptable diluents or carriers and/or surface-active agents (i.e. diluents or carriers or surface-active agents of the type generally accepted in the art as being suitable for use in herbicidal composition and which are compatible with the phenoxypicolinamide compound of formula (I) and the partner herbicide). The term "homogeneously dispersed" is used to include compositions in which the phenoxypicolinamide compound of formula (I) and the partner herbicide are dissolved or dispersed in the other components. The term "herbicidal compositions" is used in a broad sense to include not only compositions which are ready for use as herbicides but also concentrates which must be diluted before use. Preferably, the compositions contains from 0.05% to 90% by weight of the compound of formula (I) and the partner herbicide.

The compositions preferably comprise the phenoxypicolinamide compound of formula (I) in proportions of preferably from 1:200 to 2:1, more preferably from 1:13.3 to 1:1 wt/wt of (a) to urea herbicide; from 1:13.3 to 100:1, more preferably from 1:6.7 to 25:1 wt/wt of (a) to isoxazole or dione herbicide; and from 1:66.7 to 10:1, more preferably from 1:40 to 2.5:1 wt/wt of (a) to HBN herbicide.

The herbicidal compositions may contain both a diluent or carrier and a surface-active (e.g. wetting, dispersing, or emulsifying) agent. Surface-active agents which may be present in herbicidal compositions of the present invention may be of the ionic or no-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl-sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the phenoxypicolinamide compound of formula (I) and the partner herbicide with solid diluents or by impregnating the solid diluents or carriers with solutions of the phenoxypicolinamide compound of formula (I) and a partner herbicide in volatile solvents, evaporating the solvents and, if necessary, grinding the products so as to obtain powders. Granular formulations may be prepared by absorbing the phenoxypicolinamide compound of formula (I) and a partner herbicide (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toulene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the phenoxypicolinamide compound of formula (I) and a partner herbicide may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of the phenoxypicolinamide compound of formula (I) and a partner herbicide, from 2 to 10% w/v of surface-active agent, from 0.1 to 5% w/v of thickener and from 15 to 87.9% by volume of water; wettable powders which comprise from 10 to 90% w/w of the phenoxypicolinamide compound of formula (I) and a partner herbicide, from 2 to 10% w/w of surface-active agent and from 10 to 88% w/w of solid diluent or carrier; liquid water soluble concentrates which comprise from 10 to 30% w/v of the phenoxypicolinamide compound of formula (I) and a partner herbicide, from 5 to 25% w/v of surface-active agent and from 45 to 85% by volume of water-miscible solvent, e.g. dimethylformamide; liquid emulsifiable suspension concentrates which comprise 10 to 70% w/v of the phenoxypicolinamide compound of formula (I) and a partner herbicide, from 5 to 15% w/v of surface-active agent, from 0.1 to 5% w/v of thickener and from 10 to 84.9% by volume or organic solvent; granules which comprise from 2 to 10% w/w of the phenoxypicolinamide compound of formula (I) and a partner herbicide, from 0.5 to 2% w/w of surface-active agent and from 88 to 97.5% of granular carrier and emulsifiable concentrates which comprise from 0.05 to 90% w/v, and preferably from 1 to 60% w/v, of the phenoxypicolinamide compound of formula (I) and a partner herbicide, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the phenoxypicolinamide compound of formula (I) and a partner herbicide in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example 2,4-D which is [2,4-dichlorophenoxy-acetic acid], bifenox, which is methyl 5-(2,4-dichlorophenoxy)-2-nitrobenzoate, ET-037 which is isopropyl 2-chloro-5-[4-chloro-5-(1,1-difluoromethoxy)-1-methyl-1H-pyrazol-3-yl]-4-fluorobenzoate, fenoxaprop-P-ethyl, which is ethyl (R)-2-[4-(6-chloro-1,3-benzoxazol-2-yloxy)phenoxy]propionic acid, florasulam, which is 2',4,6'-trifluoro-7-methoxy[1,2,4]triazolo[1,5-c]pyrimidine-2-sulfonanilide, fluoxypyr, which is 4-amino-3,5-dichloro-6-fluoro-2-pyridyloxyacetic acid, flurtamone, which is 5-(methylamino)-2-phenyl-4-[3-(trifluoromethyl)phenyl]-3(2H)-furanone, imazosulfuron, which is 1-(2-chloroimidazo[1,2-a]pyridin-3-ylsulfonyl)-3-(4,6-dimethoxypyrimidin-2-yl)urea, fluazolate, which is 5-[4-bromo-1-methyl-5-(trifluoromethyl)-1H-pyrazol-3-yl]-2-chloro-4-fluorobenzoic acid isopropyl ester, mecoprop P, which is [(±)-2-(4-chloro-2-methylphenoxy)propionic acid], metsulfuron-methyl, which is 2-(4-methoxy-6-methyl-1,3,5-triazin-2-ylcarbamoylsulfamoyl)benzoic acid, pendimethalin, which is N-(1-ethylpropyl)-2,6-dinitro-3,4-xylidine, quinmeric, which is 7-chloro-3-methyl-8-quinoline carboxylic acid, triallate, which is [S-2,3,3-trichloroallyl N,N-diisopropyl-(thiocarbamate)]

and trifluralin, which is [2,6-dinitro-N,N-dipropyl-4-trifluoromethylaniline].

Other biologically active materials which may be included in, or used in conjunction with, the herbicidal compositions of the present invention are plant growth regulators, e.g. succinamic acid, (2-chloroethyl) trimethylammonium chloride and 2-chloroethane-phosphonic acid; or fertilisers, e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilised in the form of conventional derivatives, for example alkali metal and amine salts and esters.

The compositions of the invention may be made up as an article of manufacture comprising the phenoxypicolinamide compound of formula (I) and a partner herbicide and optionally other pesticidally active compounds as hereinbefore described or, as is preferred, a herbicidal composition as hereinbefore described or, and preferably a herbicidal concentrate which must be diluted before use, comprising the phenoxypicolinamide compound of formula (I) and a partner herbicide within a container for the aforesaid phenoxypicolinamide compound of formula (I) and a partner herbicide or a said herbicidal composition, and instructions physically associated with the aforesaid container setting out the manner in which the aforesaid phenoxypicolinamide compound of formula (I) and a partner herbicide or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application of for example from 15 g and 1000 g of the phenoxypicolinamide compound of formula (I) and for example from 0.005 kg and 3 kg of a partner herbicide per hectare in the manner and for the purposes hereinbefore described.

According to a further feature of the present invention, there is provided a product comprising (a) a phenoxypicolinamide compound of formula (I) and (b) a partner herbicide selected from the group consisting of isoxazoles, diones, ureas and hydroxybenzonitrile herbicides as a combined preparation for simultaneous, separate or sequential use in controlling the growth of weeds at a locus.

The following is an example of a herbicidal composition suitable for use in the method for controlling the growth of weeds according to the present invention.

In the description that follows the following are trade marks;

REAX, Sellogen, Barden, Aerosil and Compound A is the phenoxypicolinamide compound of formula (I).

EXAMPLE C1

The following composition was prepared as a wettable dispersible granule (the percentages that follow are by weight):

| Compound A | 75.0% |
|---|---|
| REAX 88A (surfactant) | 10.0% |
| Sellogen HR (surfactant) | 3.0% |
| Barden AG-1 (clay) | 11.0% |
| Aerosil R972 (silica filler) | 1.0% |

This may be used in tank mixtures with partner herbicides selected from isoxazoles, diones, ureas and hydroxybenzonitrile herbicides.

In accordance with the usual practice (and a preferred method according to the present invention) a tank mix may be prepared prior to use by combining separate formulations of the individual herbicidal components.

I claim:

1. A method for controlling the growth of weeds at a locus which comprises applying to the locus a herbicidally effective amount of:

(a) a phenoxypicolinamide derivative of formula I;

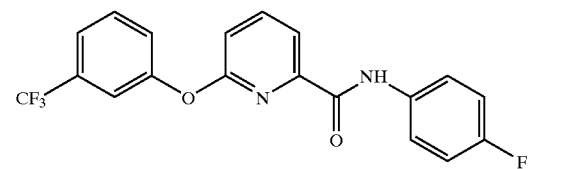

(I)

and (b) a partner herbicide selected from an isoxazole, dione, urea and hydroxybenzonitrile herbicide.

2. A method according to claim 1 in which the partner herbicide is selected from isoxaflutole, ketospirodox, mesotrione, sulcotrione, isoproturon, bromoxynil and ioxynil.

3. A method according to claim 1 in which the partner herbicide is selected from isoxaflutole, isoproturon and bromoxynil.

4. A method according to claim 1 in which the application rate of the phenoxypicolinamide herbicide is from 15 g to 500 g/ha.

5. A method according to claim 1 in which the application rate of the urea herbicide is from 250 g to 3000 g/ha.

6. A method according to claim 1 in which the application rate of the isoxazole or dione herbicide is from 5 g to 200 g/ha.

7. A method according to claim 1 in which the application rate of the hydroxybenzonitrile herbicide is from 50 g to 1000 g/ha.

8. A method according to claim 1 in which the crop is a cereal crop.

9. A method according to claim 8 in which the crop is an autumn-sown cereal.

10. A method according to claim 1 in which the weight ratio of phenoxypicolinamide herbicide: urea herbicide is from 1:200 to 2:1.

11. A method according to claim 1 in which the weight ratio of phenoxypicolinamide herbicide: isoxazole or dione herbicide is from 1:13.3 to 100:1.

12. A method according to claim 1 in which the weight ratio of phenoxypicolinamide herbicide hydroxybenzonitrile herbicide is from 1:66.7 to 10:1.

13. A method according to claim 1 in which the application rate of the phenoxypicolinamide herbicide is from 30 g to 200 g/ha.

14. A method according to claim 1 in which the application rate of the urea herbicide is from 500 g to 2000 g/ha.

15. A method according to claim 1 in which the application rate of the isoxazole or dione herbicide is from 20 g to 100 g/ha.

16. A method according to claim 1 in which the application rate of the hydroxybenzonitrile herbicide is from 200 g to 600 g/ha.

17. A method according to claim 1 in which the weight ratio of phenoxypicolinamide herbicide: urea herbicide is from 1:13.3 to 1:1.

18. A method according to claim 1 in which the weight ratio of phenoxypicolinamide herbicide: isoxazole or dione herbicide is from 1:6.7 to 25:1.

19. A method according to claim 1 in which the weight ratio of phenoxypicolinamide herbicide hydroxybenzonitrile herbicide is from 1:40 to 2.5:1.

20. A herbicidal composition comprising (a) a phenoxypicolinamide compound of formula (I) as defined in claim 1 and (b) a partner herbicide selected from an isoxazole, dione, urea and hydroxybenzonitrile herbicide, in association with an agriculturally acceptable diluent or carrier and/or surface active agent.

21. A herbicidal composition according to claim 20 which comprises 0.05 to 90% by weight of active ingredient.

22. A herbicidal composition according to claim 20, which is in liquid form and contains from 0.05 to 25% of surface-active agent.

23. A herbicidal composition according to claim 20, in the form or an aqueous suspension concentrate, a wettable powder, a water soluble or water dispersible powder, a liquid water soluble concentrate, a liquid emulsifiable suspension concentrate, a granule or an emulsifiable concentrate.

24. A product comprising a phenoxypicolinamide compound as defined in claim 1 and a partner herbicide selected from isoxazoles, diones, ureas and hydroxybenzonitrile for simultaneous, separate or sequential application in controlling the growth of weeds.

* * * * *